(12) United States Patent
Kerr

(10) Patent No.: US 11,066,139 B2
(45) Date of Patent: Jul. 20, 2021

(54) DETERMINING THE PARTIAL PRESSURE OF A GAS IN A PRESSURE VESSEL

(71) Applicant: Fathom Systems Limited, Aberdeen (GB)

(72) Inventor: Gareth Kerr, Aberdeen (GB)

(73) Assignee: FATHOM SYSTEMS LIMITED, Aberdeen (GB)

( * ) Notice: Subject to any disclaimer, the term of this patent is extended or adjusted under 35 U.S.C. 154(b) by 1191 days.

(21) Appl. No.: 15/307,483

(22) PCT Filed: Apr. 28, 2015

(86) PCT No.: PCT/GB2015/051240
§ 371 (c)(1),
(2) Date: Oct. 28, 2016

(87) PCT Pub. No.: WO2015/166234
PCT Pub. Date: Nov. 5, 2015

(65) Prior Publication Data
US 2017/0050711 A1    Feb. 23, 2017

(30) Foreign Application Priority Data
May 2, 2014   (GB) ..................................... 1407751

(51) Int. Cl.
*B63C 11/18*   (2006.01)
*B63C 11/32*   (2006.01)
(Continued)

(52) U.S. Cl.
CPC ............ *B63C 11/18* (2013.01); *A61G 10/026* (2013.01); *A62B 7/02* (2013.01); *A62B 9/006* (2013.01);
(Continued)

(58) Field of Classification Search
CPC ........ A61M 16/00; A61M 16/06–0694; A61M 16/20–209; A61M 16/0003–0012;
(Continued)

(56) References Cited

U.S. PATENT DOCUMENTS 3,593,735 A   7/1971 Reiher
4,362,154 A   12/1982 Le Masson
(Continued)

FOREIGN PATENT DOCUMENTS

CN   103884750   6/2014
EP   0270088    6/1988
(Continued)

OTHER PUBLICATIONS

International Search Report and Written Opinion for PCT/GB2015/051240 filed Apr. 28, 2015, and mailed from the International Searching Authority on Aug. 28, 2015, 8 pgs.
(Continued)

*Primary Examiner* — Jan Christopher L Merene
*Assistant Examiner* — Ned T Heffner
(74) *Attorney, Agent, or Firm* — Stoel Rives LLP

(57) ABSTRACT

There is disclosed a method and system for determining the partial pressure of at least one gas in a mixture of gasses contained in a pressure vessel, in particular a pressure vessel in the form of a life support pressure chamber/decompression chamber, or a diving gas storage cylinder. The method comprises the steps of: coupling a gas analysis sensor (14) to a pressure vessel (10); directing a portion of the mixture of gasses in the pressure vessel to the sensor for analysis; reducing the pressure of the portion of the mixture which is to be analysed by the sensor to a level which is below the pressure in the vessel but above local atmospheric pressure; operating the sensor to measure the partial pressure of the at least one gas at the reduced pressure level; and using the
(Continued)

partial pressure of the at least one gas, measured at the reduced pressure level, to determine the actual partial pressure of said gas in the mixture contained in the vessel.

17 Claims, 3 Drawing Sheets

(51) Int. Cl.
    *G01N 7/00*         (2006.01)
    *G01N 33/00*       (2006.01)
    *A62B 7/02*         (2006.01)
    *A61G 10/02*       (2006.01)
    *A62B 9/00*         (2006.01)
    *G01N 1/22*         (2006.01)

(52) U.S. Cl.
    CPC .............. *B63C 11/325* (2013.01); *G01N 7/00* (2013.01); *G01N 33/0011* (2013.01); *G01N 33/0016* (2013.01); *A61G 2203/34* (2013.01); *G01N 2001/2238* (2013.01)

(58) Field of Classification Search
    CPC ... A61M 2016/0015–0042; A61M 2016/0661; A62B 9/00; A62B 7/00; A62B 7/14; A62B 7/02; B63C 11/12; B63C 11/18; B63C 2011/188; B64D 2231/00
    See application file for complete search history.

(56) References Cited

U.S. PATENT DOCUMENTS

| | | | |
|---|---|---|---|
| 5,924,418 A * | 7/1999 | Lewis | B63C 11/24 128/204.22 |
| 2004/0107965 A1 * | 6/2004 | Hickle | A61M 16/0051 128/204.22 |
| 2006/0107898 A1 | 5/2006 | Blomberg | |

FOREIGN PATENT DOCUMENTS

| | | |
|---|---|---|
| EP | 2080017 | 5/2008 |
| EP | 2088424 A1 | 12/2009 |
| GB | 2094483 | 9/1982 |
| NL | 1011892 C2 | 10/2000 |
| WO | 20080055167 | 5/2008 |

OTHER PUBLICATIONS

International Preliminary Report on Patentability for Application No. PCT/GB2015/051230 filed Apr. 28, 2015, and mailed from the International Bureau on Nov. 17, 2016, 4 pgs.

* cited by examiner

DETERMINING THE PARTIAL PRESSURE OF A GAS IN A PRESSURE VESSEL

RELATED APPLICATIONS

This application is the U.S. National Stage filing under 35 U.S.C. § 371 of International Patent Application No. PCT/GB2015/051240, filed on Apr. 28, 2015 and titled DETERMINING THE PARTIAL PRESSURE OF A GAS IN A PRESSURE VESSEL, which claims the benefit of Great Britain Patent Application No. 1407751.5, filed on May 2, 2014 and titled DETERMINING THE PARTIAL PRESSURE OF A GAS IN A PRESSURE VESSEL, each of which is incorporated herein by reference in its entirety.

The present invention relates to a method and system for determining the partial pressure of at least one gas in a mixture of gasses contained in a pressure vessel. In particular, but not exclusively, the present invention relates to a method and system for determining the partial pressure of at least one gas in a mixture of gasses contained in a pressure vessel in the form of a life support pressure chamber/decompression chamber, or in the form of a gas storage cylinder (which may be a diving gas storage cylinder, from which pressurised breathing gas is conveyed to a diver's breathing apparatus via a suitable pipe/hose).

Divers operating at depth in a body of water experience elevated pressures. On average, the pressure in a body of water increases by 1 atmosphere (atm), or 1.01325 bar, for every 10 metres sea water (msw) in depth. Consequently, a diver operating at a depth of 100 msw will experience a pressure of 10 atm (10.1325 bar), at 200 msw a pressure of 20 atm (20.265 bar), and so on.

Under pressure at depth, increased volumes of gasses pass into solution in a diver's body. This effect tends to occur at an exponential rate depending upon the difference between the external gas partial pressures, the solubility of the breathed gasses and the partial pressures of the gases already dissolved in the body. Therefore the majority of the gasses (at a given depth) pass into solution quickly, with the rate of absorption reducing over time, until equilibrium is reached, when external and dissolved gas partial pressures are equal and no more gas goes into solution. Once equilibrium has been reached the diver is saturated and the practice of diving in this condition is known as saturation diving.

It is for this reason that divers have to ascend from depth slowly and, depending upon their depth and time of exposure to pressure, often have to stop at particular depths during their ascent to the surface. These stops, coupled with slow ascent, enable the dissolved gasses to come out of solution through the lungs, and the differential pressures between the dissolved gases in the diver's body and the external pressure is sufficiently low so that damaging bubbles do not form in the body. When saturation diving, divers have to remain at pressure for the entire duration of the dive, which may last for several weeks. To accomplish this, the divers live in pressurised chambers on the surface, and are transported to and from depth in a pressurised diving bell. A single process of stops and ascent occur at the end of the saturation dive. This is more efficient than doing a series of repeated short duration dives, where the combined durations of decompression would be much greater.

Atmospheric air is a mixture of gasses, which typically contains approximately 78% Nitrogen ($N_2$) and 21% Oxygen ($O_2$). The partial pressure of each gas in the mixture is the hypothetical pressure of that gas if it alone occupied the volume of the mixture at the same temperature. Accordingly, at a standard surface pressure of 1 atm, the partial pressure of $O_2$ is typically 0.21 atm or ~0.20265 bar. At a depth of 100 msw, the partial pressure of $O_2$ would therefore be 2.1 atm (~2.0265 bar), and at 200 msw would be 4.2 atm (~4.053 bar).

Divers operating at shallow depths for short periods employ a breathing gas which is often simply compressed air. However, divers descending to greater depths, and/or operating underwater for longer periods, have to use specialised breathing gas mixtures. This is for various reasons. Firstly, it is known that $N_2$ under pressure has a narcotic effect, which dangerously impairs performance. These effects commence at a depth of around 40 m, and become worse with increased depth (and so pressure). Accordingly, Helium (He), which does not have a narcotic effect, is used in place of $N_2$. Secondly, it is well known that the proportion of the various gasses in a diver's breathing gas must be carefully controlled, in order to prevent certain harmful effects. In particular, $O_2$ is toxic at elevated partial pressures, depending upon the length of exposure and the partial pressure. For long term exposures, the partial pressure of $O_2$ must be kept to below 0.5 bar, and typically in the range of 0.44 bar to 0.48 bar during storage in a pressure chamber, and 0.40-0.60 bar for in-water excursions of a few hours. Similarly, the partial pressure of Carbon Dioxide ($CO_2$) must be kept to below 0.005 bar, above which level the gas is toxic. In addition, and in particular where gases in the pressurised system are re-cycled, there may be other gases present in trace amounts that should be measured. These may include Carbon Monoxide, residual Nitrogen and Argon.

A diver whose body has become saturated with gasses at a particular pressure (and so depth) must spend around 1 day decompressing in a decompression chamber per 30 msw of operating depth. Consequently, a diver who has operated at a depth of 150 msw for a sufficiently long period of time for his body to become saturated with gasses (at that pressure) must decompress for 5 days, whilst a diver operating at depths of up to 300 msw would need to decompress for around 10 days.

Accordingly, divers have to spend significant amounts of time under pressure in the water and inside pressure chambers, during rest periods between deployment underwater, and also during subsequent decompression. When under pressure, the constituents of divers' breathing gas have to be kept within accurate limits, in order to avoid the problems discussed above. Since the partial pressure of the gasses is related to the pressure in the chamber and the proportion of the gas in the breathing mixture, at high pressures the actual proportion of gas (to be measured) in the mixture can be very small. For example, a diver operating at a depth of 100 msw (i.e. 10.1325 bar) for a sustained period will be provided with breathing gas in which the partial pressure of $O_2$ at that depth will be kept to around 0.48 bar, as discussed above. As a result, at surface atmospheric pressure, the partial pressure of $O_2$ in the mixture will be only 0.0474 bar by volume, which equates to just ~4.74% of the total. For a depth of 200 msw (20.265 bar), the partial pressure of $O_2$ will be only 0.0237 bar, equating to just ~2.37%, by volume, of the total.

This presents a significant problem to the safe operation of diving systems, because the partial pressures of the gasses in the breathing mixture must be accurately measured, so that the relative proportions of the gasses can be accurately controlled. The difficulty is that the sensors which are used to measure the partial pressure of the gasses in the breathing gas mixture have to be located outside of the pressure chamber, so that they can be accessed for periodic calibration using a dedicated calibration gas, the constituents of which are precisely known. More significantly, prior to passing through the sensor, the breathing gas is de-pressurised to local atmospheric pressure.

Since the partial pressure of the gas component being analysed is related to the overall pressure of the mixture, the measured values will reduce in proportion to the ratio of the pressure in the system to the pressure at which the measurement is made. The raw outputs from the sensors used to measure $O_2$ and $CO_2$ are proportional to the partial pressure of the gas in the mixture measured at the sensor (at atmospheric pressure), and if proportional (percentage) readings are required corresponding to the partial pressure of that gas in the system, the partial pressure value has to factored to eliminate the effects of pressure. This is achieved by measuring the pressure inside the system.

Using an extreme example of a working pressure equivalent to 300 msw (30 atm or 30.3975 bar), and using the maximum allowable $CO_2$ partial pressure given above (0.005 bar), the measured partial pressure of $CO_2$ in the breathing gas mixture at atmospheric pressure will be just 0.00016 bar (or ~0.016% by volume of the mixture total, at atmospheric pressure). The partial pressure band for oxygen would be measured to be just 0.015 bar to 0.016 bar (or ~1.48% to 1.58% $O_2$ by volume of the mixture total, at atmospheric pressure). This is a significant problem because, in order to accurately measure the proportions of $CO_2$ and $O_2$ in the mixture, sensor resolution and accuracy needs to be superior to the magnitude of the quantity being measured. In addition, typical sensors may only have an accuracy of only around ±2%, with the result that they cannot accurately measure the proportions of $CO_2$ and $O_2$ in the mixture.

From the above, it can be seen that diver safety depends upon being able to measure these partial pressures very accurately. It can also be seen that the requirement for accuracy becomes more onerous as pressure increases, and that for deep (high pressure) diving, very accurate instruments are needed.

Whilst reference is made particularly to problems associated with divers operating under pressure at depth, it will be understood that the problems associated with working under pressure, and the safe operation of pressure chambers, is not restricted to divers. Many other workers operate at pressure, including but not restricted to construction workers operating at elevated pressures in caissons and tunnels. Pressure chambers are also commonly used in the healthcare industry, for a variety of hyperbaric treatments.

It is amongst the objects of the present invention to obviate or mitigate at least one of the foregoing disadvantages.

According to a first aspect of the present invention, there is provided a method of determining the partial pressure of at least one gas in a mixture of gasses contained in a pressure vessel, the mixture being pressurised to above local atmospheric pressure, in which the method comprises the steps of:

coupling a gas analysis sensor to the pressure vessel;
directing a portion of the mixture of gasses in the pressure vessel to the sensor for analysis;
reducing the pressure of the portion of the mixture which is to be analysed by the sensor to a level which is below the pressure in the vessel but above local atmospheric pressure;
operating the sensor to measure the partial pressure of the at least one gas at the reduced pressure level; and
using the partial pressure of the at least one gas, measured at the reduced pressure level, to determine the actual partial pressure of said gas in the mixture contained in the vessel.

In the method of the present invention, the partial pressure is measured at a pressure level of the mixture which is below the pressure in the vessel. In this way, it is not necessary to provide a sensor capable of operating under the relatively high pressures found in the pressure vessel. However, the pressure level is above that of local atmospheric pressure. This provides a significant advantage over the prior method. In particular, measuring the partial pressure of the mixture at a level which is above local atmospheric pressure has the effect of increasing the sensitivity, resolution and potentially also the signal to noise ratio of the sensor/system employing the sensor. This can provide significant improvements in the accuracy of the partial pressure of the gas which is determined employing the partial pressure measured by the sensor.

Accordingly, instead of allowing the vessel gas to depressurise to atmospheric pressure before taking measurements (as with the prior method), the method of the present invention involves maintaining some pressure (above local atmospheric) at the sensor, providing improved accuracy in proportion to the ratio of the raised pressure to atmospheric pressure. For example, if the pressure at the sensor is maintained at 2 bar (instead of e.g. 1 bar local atmospheric pressure), then the measured partial pressure will be twice as large, with equivalent improvement in measurement accuracy of the sensor.

Reference is made herein to local atmospheric pressure. It will be understood that, in the context of the invention, such should be taken to be the prevailing atmospheric (or barometric) pressure of the air in the region of the sensor. It is well known that atmospheric pressure varies, dependent upon factors including atmospheric conditions and height above sea level. Indeed, local atmospheric pressure may be above or below 'standard' atmospheric pressure, which is taken to be 1.01325 bar.

The method may comprise locating the sensor outside the vessel, and the step of directing the portion of the mixture to the sensor for analysis may comprise directing the portion of the mixture out of the vessel to the sensor.

The step of reducing the pressure of the portion of the mixture which is to be analysed may comprise reducing the pressure prior to supply of the portion of the mixture to the sensor, such as to an input of the sensor. The pressure may be reduced employing a pressure control device such as a pressure reduction valve, and the method may comprise arranging the pressure control device to provide an output at a predetermined or selected pressure level.

The step of reducing the pressure of the portion of the mixture which is to be analysed may comprise reducing the pressure within the sensor prior to analysis. The pressure may be reduced employing a pressure control device, such as a pressure reduction valve, provided integrally with the sensor.

The method may comprise controlling a rate of flow of the portion of the mixture through the sensor. The rate of flow may be controlled using a throttle, such as a throttle valve.

The method may comprise throttling the flow of the mixture upstream of the sensor. The pressure of the portion of the mixture may then be controlled using a back-pressure regulator downstream of the throttle, and which may be located downstream of the sensor. The back-pressure regulator may account for any pressure losses which occur during throttling, ensuring the pressure of the mixture to be measured by the sensor is at the desired level.

The method may comprise throttling the flow of the mixture downstream of the sensor. In this way, any pressure losses which occur during throttling may not affect the pressure of the mixture to be measured by the sensor.

The pressure of the portion of the mixture which is to be analysed may be reduced to one that provides a balance of increased sensor complexity (due to the requirement to support higher pressures) relative to the improved accuracy of the measurement which is achieved. The pressure of the portion of the mixture which is to be analysed may be reduced to no less than about 1.5 times local atmospheric pressure. The pressure of the portion of the mixture which is to be analysed may be reduced to no less than about 2 times local atmospheric pressure. The pressure of the portion of the mixture which is to be analysed may be reduced to no less than about 3 times local atmospheric pressure. The pressure of the portion of the mixture which is to be analysed may be reduced to no more than about 4 times local atmospheric pressure. The level of pressure selected may be anywhere between about 1.5 to about 4 times local atmospheric pressure. A pressure level within this range may provide a balance of increased sensor cost (due to the requirement to support higher pressures) relative to the improved accuracy of the measurement which is achieved. The level of pressure which is selected may be dependent on factors including: the pressure of the mixture in the vessel; the maximum operating pressure of the sensor; the sensitivity of the sensor; the resolution of the sensor; and/or the signal to noise ratio of the sensor/system employing the sensor.

The step of using the partial pressure of the at least one gas to determine the actual partial pressure of said gas in the vessel may involve multiplying the measured pressure (at the reduced pressure level) by the ratio of the pressure in the vessel relative to the reduced pressure level. It can therefore be seen that an improvement in the accuracy of the measurement taken by the sensor will lead to an improvement in the accuracy of the partial pressure of the at least one gas in the vessel, determined employing that measurement.

The method may comprise determining the partial pressures of a plurality of gasses in the mixture of gasses in the vessel. The sensor may be used to measure the partial pressures of a plurality of gasses, or a plurality of sensors may be employed, each sensor measuring the partial pressure of a single gas. The mixture of gasses may be a breathable mixture containing $CO_2$, $O_2$ and which may contain a diluent gas such as He, and other trace gases such as Carbon Monoxide, Nitrogen and Argon at very small concentrations. The method may comprise determining the partial pressures of $CO_2$, $O_2$, trace gases and/or the diluent gas in the mixture of gasses in the vessel.

The pressure vessel may be maintained at a substantially constant pressure over a determined period of time. Such may be the case where the pressure vessel is a pressure chamber providing life support for divers for long periods of time (of the order of days), in between periods where the divers operate underwater at depth. The pressure chamber may therefore be a life support pressure chamber, and may be a diving life support pressure chamber. The pressure chamber may be a diving bell.

The pressure chamber may additionally or alternatively function as a decompression chamber, in which the pressure of the mixture of gasses in the chamber is reduced over time in a controlled fashion, employing the determined partial pressure data. Thus the method may comprise reducing the pressure of the mixture in the chamber over time, to decompress a person or persons (e.g. divers) from the raised pressure in the chamber (which is set according to the pressure under which the person has been operating) to local atmospheric pressure. The method may comprise maintaining the level of the pressure of the mixture to be analysed substantially constant during a substantial part of the decompression period, and may involve maintaining said level substantially constant at least until the pressure in the chamber has reduced to or near the pressure level at which the measurement is taken.

The pressure vessel may be a gas storage tank or cylinder, in particular a diving gas storage cylinder. The method may comprise directing the mixture of gasses in the cylinder to a diver; performing an initial reduction in the pressure of the mixture of gases directed from the cylinder to the diver to a level which is determined according to an operating depth of the diver; and then directing the portion of the mixture of gasses to the sensor (at the initially reduced pressure level).

Determination of the actual partial pressure of the at least one gas in the mixture contained within the vessel (or other pressurised parts of a pressurised system including the vessel) may enable determination of the proportion of said gas in the mixture. The method may comprise determining the partial pressure of a plurality of gasses in the mixture, optionally of the gas or gasses making up a majority of the mixture. This may facilitate determination of the composition of the mixture of gasses contained in the vessel.

According to a second aspect of the present invention, there is provided a method of controlling the partial pressure of at least one gas in a mixture of gasses contained in a pressure vessel, the method comprising:

determining the partial pressure of the at least one gas in the mixture following the method of the first aspect of the present invention;

and then varying the proportion of the at least one gas in the mixture in the vessel in order to maintain the partial pressure of said gas within a target pressure range.

The method may be a method of providing life support for a person operating under pressure (e.g. underwater), in which the mixture of gasses in the chamber is a breathable mixture. The method may be a method of decompressing a person from a pressure which is above local atmospheric pressure (at which the person has been operating e.g. underwater) down to local atmospheric pressure. The method may be a method of providing life support for a person operating under pressure (e.g. underwater), in which the mixture of gasses is supplied, under pressure, to a person's breathing apparatus.

Further features of the step of determining the partial pressure of the at least one gas may be derived from the text set out above relating to the first aspect of the invention.

According to a third aspect of the present invention, there is provided a gas analysis system for a pressure vessel, for determining the partial pressure of at least one gas in a mixture of gasses contained in the pressure vessel, the mixture being pressurised to above local atmospheric pressure, in which the system comprises:

a gas analysis sensor which can be coupled to the pressure vessel so that a portion of the mixture of gasses in the pressure vessel can be directed to the sensor for analysis; and a pressure control device for reducing the pressure of the portion of the mixture which is to be analysed by the sensor;

in which, in use:
the pressure control device is arranged to reduce the pressure of the portion of the mixture to a level which is below the pressure in the vessel but above local atmospheric pressure; and
the sensor is arranged to measure the partial pressure of the at least one gas at the reduced pressure level, so that the partial pressure of the at least one gas measured at the reduced pressure level can be employed to determine the actual partial pressure of said gas in the mixture contained in the vessel.

The system may be configured such that, in use: the pressure control device is arranged to reduce the pressure of the portion of the mixture to said level; and the sensor is arranged to measure the partial pressure of the at least one gas at the reduced pressure level, so that said partial pressure can be employed to determine said actual partial pressure. The system may comprise a processor or controller which is configured in this way (such as via suitable software in/carried by the processor).

The sensor may be locatable outside the vessel, and the system arranged so that the portion of the mixture to be analysed is directed out of the vessel to the sensor.

The pressure control device may be a pressure reduction valve.

The pressure control device may be arranged to reduce the pressure of the portion of the mixture prior to supply of said portion to the sensor, such as to an input of the sensor. The pressure control device may be arranged to provide an output at a predetermined or selected pressure level.

The pressure control device may be provided integrally with the sensor.

The system may comprise a flow control device for controlling a rate of flow of the portion of the mixture through the sensor. The flow control device may be a throttle, such as a throttle valve.

The flow control device may be arranged to throttle the flow of the mixture upstream of the sensor. The system may comprise a back-pressure regulator positioned downstream of the flow control device, for controlling a pressure of the portion of the mixture analysed by the sensor.

The flow control device may be arranged to throttle the flow of the mixture downstream of the sensor.

The system, in particular the pressure control device, may be arranged to reduce the pressure of the portion of the mixture which is to be analysed to no less than about 1.5 times local atmospheric pressure; no less than about 2 times local atmospheric pressure; and optionally no less than about 3 times local atmospheric pressure. The system, in particular the pressure control device, may be arranged to reduce the pressure of the portion of the mixture which is to be analysed to no more than about 4 times local atmospheric pressure. The pressure control device may be arranged so that the level of pressure selected may be anywhere between about 1.5 to 4 times local atmospheric pressure.

The system may comprise a processor for determining the actual partial pressure of said gas by multiplying the measured pressure (at the reduced pressure level) by the ratio of the pressure in the vessel relative to the reduced pressure level. This may be achieved via suitable software in/carried by the processor.

According to a fourth aspect of the present invention, there is provided a pressure vessel comprising the gas analysis system of the third aspect of the invention.

The pressure vessel may be operable to maintain the pressure of mixture at a substantially constant pressure over a determined period of time. The pressure vessel may be a pressure chamber, and may be a life support chamber, e.g. for divers operating at depth for long periods of time (of the order of days). The pressure chamber may be a diving life support pressure chamber. The pressure chamber may be a diving bell. The pressure chamber may additionally or alternatively function as a decompression chamber, in which the pressure of the mixture of gasses in the chamber can be reduced over time in a controlled fashion, employing the determined partial pressure data. The pressure vessel may be a gas storage cylinder or tank, in particular a diving gas storage cylinder.

Further features of the gas analysis system may be derived from the text set out above relating to the third aspect of the invention.

Embodiments of the present invention will now be described, by way of example only, with reference to the accompanying drawings, in which.

Figure 1:
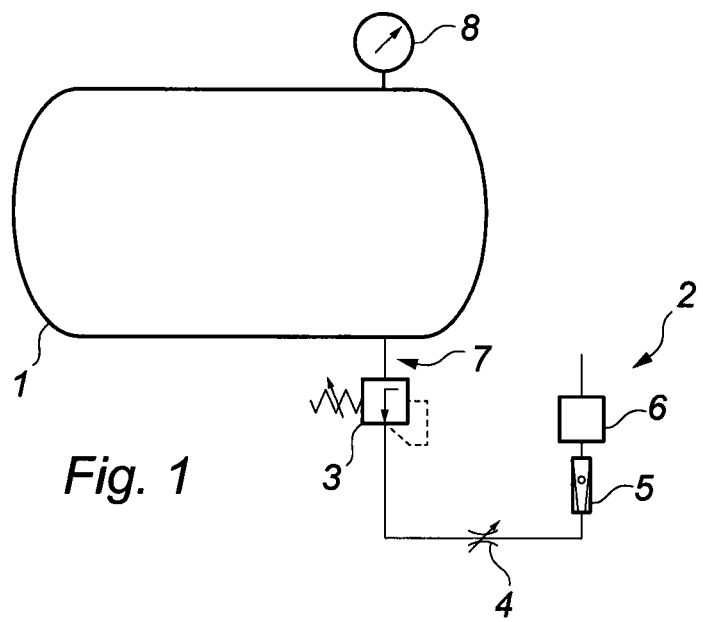
FIG. 1 is a schematic illustration of a pressure chamber with a gas analysis system of a type known in the art which is employed to determine the partial pressure of a gas in a mixture of gases contained in the pressure chamber.

Turning firstly to FIG. 1, there is shown a schematic illustration of a pressure chamber 1 incorporating a gas analysis system 2 of a type which is known in the art. The pressure chamber 1 is a life support chamber, containing a breathable mixture of gases at a pressure which is above local atmospheric pressure. The pressure chamber 1 provides life support for a person or persons who have been exposed to elevated pressures (above local atmospheric pressure) for relatively long periods of time, of the order of hours or days. Suitable examples include divers operating underwater at depths of up to around 200 msw, or even 300 msw with specialised diving equipment. The pressure chamber 1 can also be used as a decompression chamber, during subsequent decompression of a person or persons exposed to such elevated pressures.

The prior gas analysis system 2 comprises a pressure reducing valve 3, throttle valve 4, flow meter 5, gas analysis sensor 6, flow line 7 and pressure measurement device 8. The gas analysis system 2 is coupled to the pressure chamber 1 so that a portion of the mixture of gases can be exhausted from the chamber through the flow line 7, for direction to the sensor 6 for analysis. The pressure reducing valve 3 reduces the pressure of the mixture of gases directed to the sensor 6 to local atmospheric pressure level. The throttle valve 4 serves for throttling the flow of the mixtures of gases to a flow rate suitable for the gas analysis sensor 6, the flow being metered using the flow meter 5, to verify the flow rate is within a suitable range. The sensor 6 is responsive to partial pressure, and the output of the sensor is proportional to the percentage of the target gas present at atmospheric pressure. The pressure measurement device 8 is for determining the pressure inside the chamber 1, so that partial pressure inside the chamber can be calculated. The system 2 suffers from the significant disadvantages discussed above, in terms of the accuracy of the partial pressure measurement which is taken. This has a consequent impact upon the accuracy of the partial pressure of the gas in question at elevated pressure in the chamber 1, which is determined employing the measured partial pressure factoring in the chamber pressure, as described in detail above.

Figure 2:
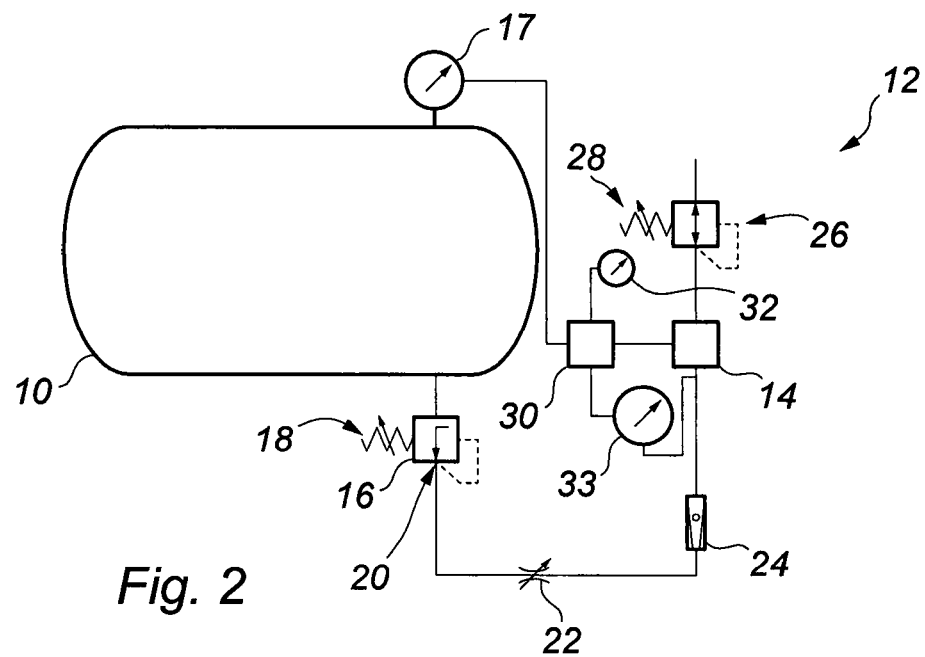
FIG. 2 is a schematic illustration of a pressure vessel, in the form of a pressure chamber, with a gas analysis system according to an embodiment of the present invention.

Turning now to FIG. 2, there is shown a schematic illustration of a pressure vessel in the form of a pressure chamber 10, having a gas analysis system according to an embodiment of the present invention, the gas analysis system indicated generally by reference numeral 12. As with the prior chamber 1 and gas analysis system 2 of FIG. 1, the pressure chamber 10 provides a life support/decompression function, particularly for a diver. The gas analysis system 12 serves for determining the partial pressure of at least one gas in a mixture of gases contained in the pressure chamber 10, where the mixture is pressurised to above local atmospheric pressure.

The gas analysis system 12 generally comprises a gas analysis sensor 14, which can be coupled to the pressure chamber 10 so that a portion of the mixture of gases in the pressure chamber can be directed to the sensor for analysis. The system 12 also comprises a pressure control device in the form of a pressure reduction valve 16, which serves for reducing the pressure of the portion of the mixture which is to be analysed by the sensor 14 to a level which is below the pressure in the chamber 10, but which is above local atmospheric pressure. The sensor 14 is operable to measure the partial pressure of the at least one gas at the reduced (mixture) pressure level, so that the partial pressure of the at least one gas measured at that reduced pressure level can be employed to determine the actual partial pressure of said gas in the mixture contained in the chamber 10, by factoring for the pressure measured at a pressure measurement device 17 (which measures the pressure inside the chamber 10).

The gas analysis sensor 14 is responsive to partial pressure, and its output is proportional to the percentage of the target gas present, factored by the ratio of the pressure above local atmospheric at which the measurement is taken, relative to standard atmospheric pressure. Standard atmospheric pressure is the accepted average atmospheric pressure, and is taken to be 1.01325 bar. The system 12 effectively internally compensates for differences between local and standard atmospheric pressure, so that a consistent benchmark is used.

For example, if the system 12 is arranged so that the pressure sensor 14 is measuring the partial pressure of the target gas at a mixture pressure which is twice that of local atmospheric pressure, then the sensor output will be twice the size of that which would be obtained if the partial pressure at the sensor were measured at local atmospheric level (assuming local atmospheric pressure is standard, i.e. 1.01325 bar). This increase in the magnitude of the output of the sensor 14 improves the accuracy, resolution and signal to noise ratio of the gas analysis system 12.

Specifically, accuracy is improved because the sensor 14 is measuring partial pressures of greater magnitude. The sensor 14 will have a particular resolution, that is a minimum pressure change step which can be detected. Measuring partial pressures of greater magnitude reduces the impact which sensor resolution has on the resulting partial pressures which are determined employing the measured partial pressure. The signal to noise ratio of the system will be dependent upon a number of factors, and is a particular issue in analogue systems employing pressure transducers, where electrical 'noise' can impact upon the measurements taken. In the prior methods, the measurement of a small partial pressure (at atmospheric level) provided a small voltage electrical output. The voltage outputs were so small that electrical noise impacted significantly on the measurement. Increasing the magnitude of the partial pressure measurement has the effect of increasing the sensor output (voltage) to outside of the range of the electrical noise.

In the gas analysis system 12 and method of the present invention, the partial pressure of the gas in question is measured at a pressure level of the mixture of gases which is below the pressure of the mixture in the pressure chamber 10. In this way, it is not necessary to provide a sensor capable of operating under the high pressures found in the pressure chamber 10. For example, pressures of up to 30 atm (30.3975 bar) may be experienced in the chamber 10. However, the pressure level at which the partial pressure is measured is above that of local atmospheric pressure, with the benefits discussed above.

The gas analysis system 12 and corresponding method of determining partial pressure will now be described in more detail.

The system 12 is configured such that, in use: the pressure control device (control valve 16) is arranged to reduce the pressure of the portion of the mixture to a level which is below the pressure in the chamber 10 but above local atmospheric pressure; and such that the sensor 14 is arranged to measure the partial pressure of the at least one gas at the reduced pressure level, so that the partial pressure of the at least one gas measured at the reduced pressure level can be employed to determine the actual partial pressure of said gas in the mixture contained in the chamber 10. To this end, the system 12 comprises a suitably configured processor or controller 30. It will be understood that this is achieved via suitable software in the processor 30.

The pressure control device 16 takes the form of a pressure reducing valve including a biased valve element 18. The valve element 18 may be of any suitable type, such as a butterfly or poppet valve element, and may be biased in any suitable way, such as via a spring. The valve element 18 is adjustable to reduce the pressure at an outlet 20 of the valve 16 to the required pressure level (which is the pressure level at which the portion of the mixture is to be supplied to the sensor for analysis). The pressure control valve 16 automatically adjusts itself to provide the desired output pressure at the outlet 20, irrespective of the supply pressure of the chamber 10. In this way, variations in the pressure in the chamber 10, and so of the supply pressure to the control valve 16, can be accounted for.

The system 12 also comprises a flow control device in the form of a throttle, typically a throttle valve 22, which controls the flow rate of the portion of the mixture of gases supplied to the sensor 14 to within the operating flow range of the sensor. The throttle 22 is adjustable, and a flow meter 24 provides verification that the flow rate is within the desired operating range. In the system 12 of FIG. 2, throttling occurs upstream of the sensor 14. There will be a pressure drop across the throttle valve 22, and so the system 12 includes a back pressure regulator 26 which is of similar structure and operation to the pressure control valve 16, and so including a biased valve element 28. The back pressure regulator 26 enables the pressure drop across the throttle valve 22 to be accounted for, setting the pressure at the sensor 14 at the desired level.

The pressure of the portion of gases which is to be analysed by the sensor 14 may be reduced to a level which is no less than about 1.5 times local atmospheric pressure, and no more than about 4 times local atmospheric pressure. A suitable operating range may be around 2 times to around 3 times local atmospheric pressure. The pressure level is selected to provide a balance of increased sensor cost (due to the requirement to support pressures above atmospheric) relative to the improved accuracy of the partial pressure which is determined employing partial pressure measurement taken by the sensor 14. The level of pressure selected may be dependent on factors including the pressure of the mixture in the chamber 10; the maximum operating pressure of the sensor 14; the sensitivity of the sensor; the resolution of the sensor; and/or the signal to noise ratio of the sensor/system. Thus pressures outside of the above ranges may be employed, depending upon numerous factors. The system 12 will factor for differences between local atmospheric and standard atmospheric pressure, as discussed above.

Taking the example of a diver operating at a depth of 100 msw for a sustained period, where a pressure of 10 atm (10.1325 bar) is experienced, the diver in the chamber 10 would be provided with breathing gas in which the partial pressure of $O_2$ would be around 0.48 bar. At local, surface atmospheric pressure, the partial pressure of $O_2$ in the mixture would be only 0.0474 bar, which equates to just ~4.74% by volume of the total. Following the prior method discussed above and shown in FIG. 1, this would represent a significant potential inaccuracy in the partial pressure measurement of $O_2$. In addition, some conventional gas analysis sensors used in prior systems are believed to only have an accuracy of around ±2%. This has a significant impact in the measurement of such small partial pressures, and so percentages (by volume) of target gasses.

In the method and system of the present invention, and taking an example of a reduction of the pressure of the mixture at the sensor 14 to 2 atm (2.0265 bar), and with local atmospheric pressure being standard and so 1 atm (1.01325 bar), the partial pressure of the gas measured by the sensor 14 will be twice as large as it would be at atmospheric pressure, with an equivalent improvement in measurement accuracy. Specifically, the partial pressure measurement at a mixture pressure of 2 atm would provide an $O_2$ partial pressure of 0.0948 bar, which is double that at atmospheric pressure. The accuracy of the sensor thus impacts to a lesser extent on the measurement taken, and so upon the partial pressure of $O_2$ in the mixture in the chamber 10 which is determined employing the partial pressure measurement.

The gas analysis system 12 and method of the present invention can be further enhanced by using a sensor 14 with a greater accuracy. Gas analysis sensors are commercially available with accuracies of ±0.1%, although this does have a corresponding impact on cost. A gas analysis sensor 14 with an accuracy of ±0.1% can provide acceptable partial pressure measurements at mixture pressures up to 150 msw, employing the prior method discussed above and shown in FIG. 1. This can effectively be doubled in the system 12 and method of the present invention, taking partial pressure measurements at mixture pressures of twice local atmospheric pressure, effectively providing the same level of accuracy down to 300 msw. Typically, the sensor 14 will be provided in a temperature controlled environment, such as a temperature controlled chamber (not shown), it being known that temperature has an impact upon pressure measurements and sensor accuracy.

The sensor 14 may be capable of measuring the partial pressures of more than one gas, or the system 12 may be provided with a plurality of dedicated sensors, each for measuring the partial pressure of a particular gas in the mixture in the chamber 10.

It will be understood that the gas analysis system 12 and method of the present invention has a use in measuring partial pressures of gases in the mixture in the chamber 10 both where the mixture pressure is held substantially constant (as would be the case where the chamber 10 is employed to provide diver support during rest periods in between times when a diver is operating underwater), as well as where the pressure in the chamber 10 is decreasing over time (as occurs during decompression). In both scenarios, the partial pressure of the gas or gases measured by the sensor 14 can be employed to determine the actual partial pressure of that gas in the mixture of gases in the chamber 10. This is of great importance particularly in relation to $O_2$ and $CO_2$, as discussed in detail above.

To this end, the system processor 30 is configured (via suitable software) so that it processes the partial pressure of the gas measured by the sensor 14. The processor 30 reads data relating to the pressure of the mixture in the chamber 10 (measured by the device 17), the pressure level at the sensor 14 (measured by a suitable sensor 33), and local atmospheric pressure (measured using a suitable sensor 32). The processor 30 determines the actual partial pressure of the target gas in the chamber 10 by multiplying the measured partial pressure by the ratio of the pressure of the mixture within the chamber relative to the (reduced) pressure level of the mixture at the sensor 14 (factoring for differences in local/standard atmospheric, if required). The data outputted by the processor 30 can then be used to appropriately alter/control the proportions of the relevant gases in the mixture in the chamber 10, if required.

Figure 3:
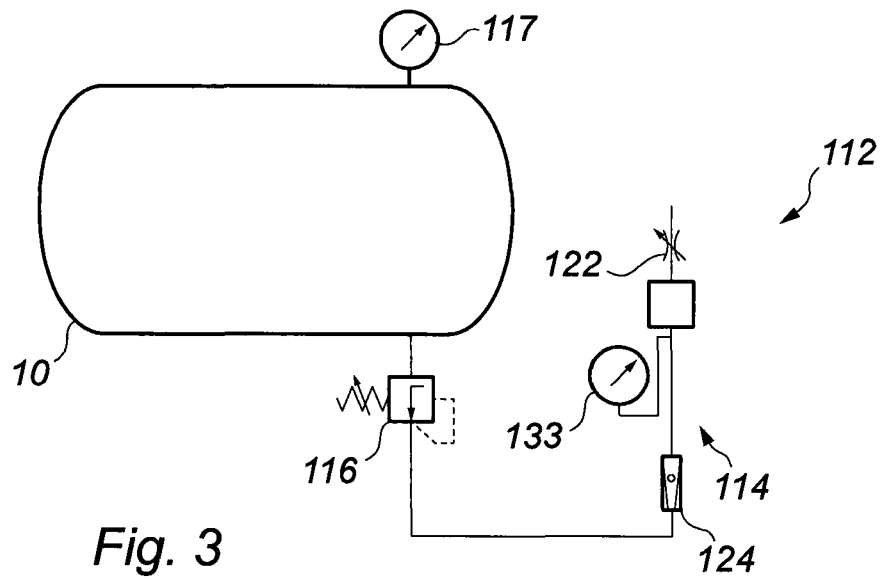
FIG. 3 is a schematic illustration of a gas analysis system in accordance with another embodiment of the invention.

Turning now to FIG. 3, there is shown a schematic illustration of a pressure chamber and gas analysis system in accordance with another embodiment of the invention, the gas analysis system indicated generally by reference numeral 112. In FIG. 3, the pressure chamber is again designated by reference numeral 10. Like components of the system 112 with the system 12 of FIG. 2 share the same reference numerals, incremented by 100.

In this embodiment, the flow of mixture of gases in the chamber 10 to a gas analysis sensor 114 is throttled downstream of the sensor 114, employing a throttle in the form of a throttle valve 122. A pressure control device in the form of pressure control valve 116 reduces the pressure of the portion of the mixture in the chamber 10 supplied to the sensor 114 for analysis. In this embodiment, as the flow is throttled downstream of the sensor 114, any pressure drop across the throttle valve 122 does not impact on the pressure of the mixture at the sensor 114. Accordingly, it is not necessary to provide a back pressure regulator such as that shown at 26 in FIG. 2. Flow through the sensor 114 is again metered using a flow meter 124. Local pressures inside the chamber and at the sensor 114 are measured using pressure measurement devices 117 and 133, and a processor (not shown) is employed to determine the partial pressure of the target gas or gasses.

Figure 4:
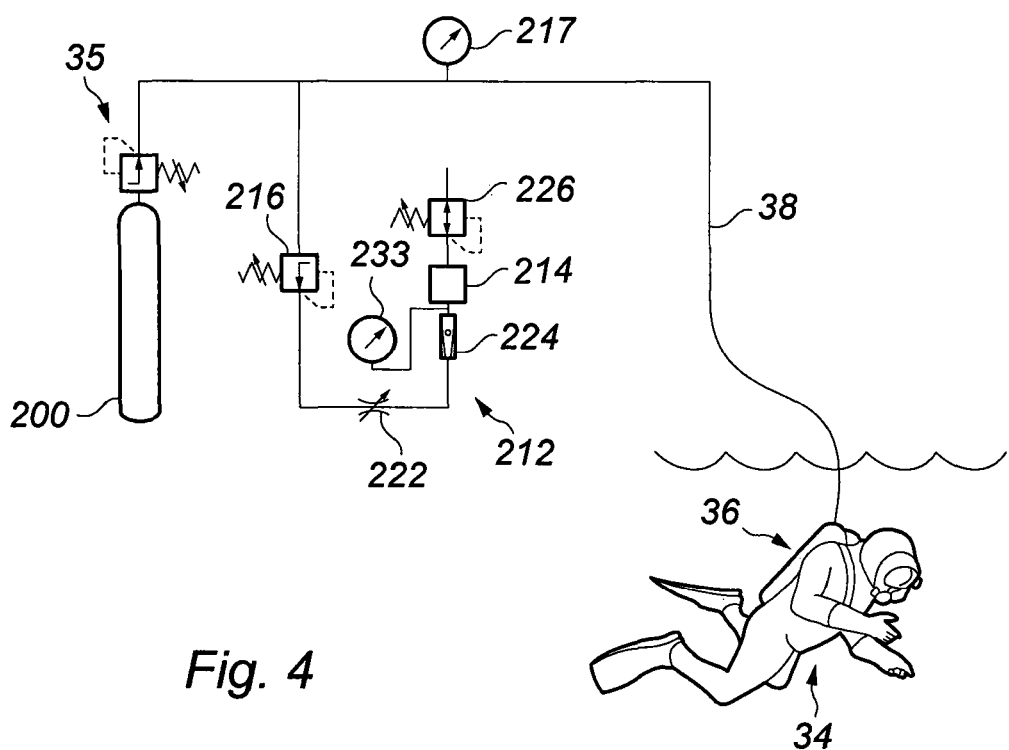
FIG. 4 is a schematic illustration of a pressure vessel, in the form of a gas storage cylinder coupled to a diver's breathing apparatus, and having a gas analysis system according to an embodiment of the present invention.

Turning now to FIG. 4, there is shown a schematic illustration of a pressure vessel and gas analysis system in accordance with another embodiment of the invention. The pressure vessel is designated by reference numeral 200, and takes the form of a gas storage cylinder or tank, which stores breathing gas for a diver 34. In this embodiment, the gas analysis system is indicated generally by reference numeral 212. Like components of the system 212 with the system 12 of FIG. 2 share the same reference numerals, incremented by 200.

The system 212 is essentially of like construction to the system 12, and operated in a similar fashion. The substantial difference between the embodiment of FIG. 4 and that of FIG. 2 is that, instead of monitoring the partial pressure of a target gas or gasses within a pressure chamber suitable for receiving e.g. the diver 34, the system 212 monitors the partial pressure of a gas/gasses in a mixture contained in the tank 200, which are supplied to breathing apparatus 36 worn by the diver via a hose 38. The system 212 is used to test the breathing gas before it goes to the diver 34 in the water.

The breathing gas is stored in the tank 200, which is a high pressure cylinder, and the pressure is reduced by a pressure control device 35 (similar to the device 16 of FIG. 2). This provides overpressure with respect to the hydrostatic pressure at the particular operating depth of the diver 34, matched to the requirement of the breathing apparatus 36 that the diver is using. Analysis takes place at 'the last point' before entering the hose 38 leading directly to the diver 34. As before, the pressure is further reduced by the system 212, to a desired level above local atmospheric, before the analysis.

The system 212 thus comprises a gas analysis sensor 214, pressure reducing valve 216, throttle valve 222, flow meter 224 and back pressure regulator 226. Pressure sensors 217 and 233 measure local atmospheric pressure and the pressure at the sensor 214, respectively. A processor (not shown) is employed to determine the partial pressure of the target gas or gasses. Effectively, the system 212 directs a portion of the mixture of gasses flowing from the tank 200 to the diver 34 (following reduction by the device 35) to the sensor 214 for analysis at a further reduced pressure level (relative to that of the mixture in the tank 200).

In a variation on the system 212 shown in FIG. 4, a system of like construction to the system 112 of FIG. 3 may be employed, where throttling occurs downstream of the sensor 214.

Figure 5:
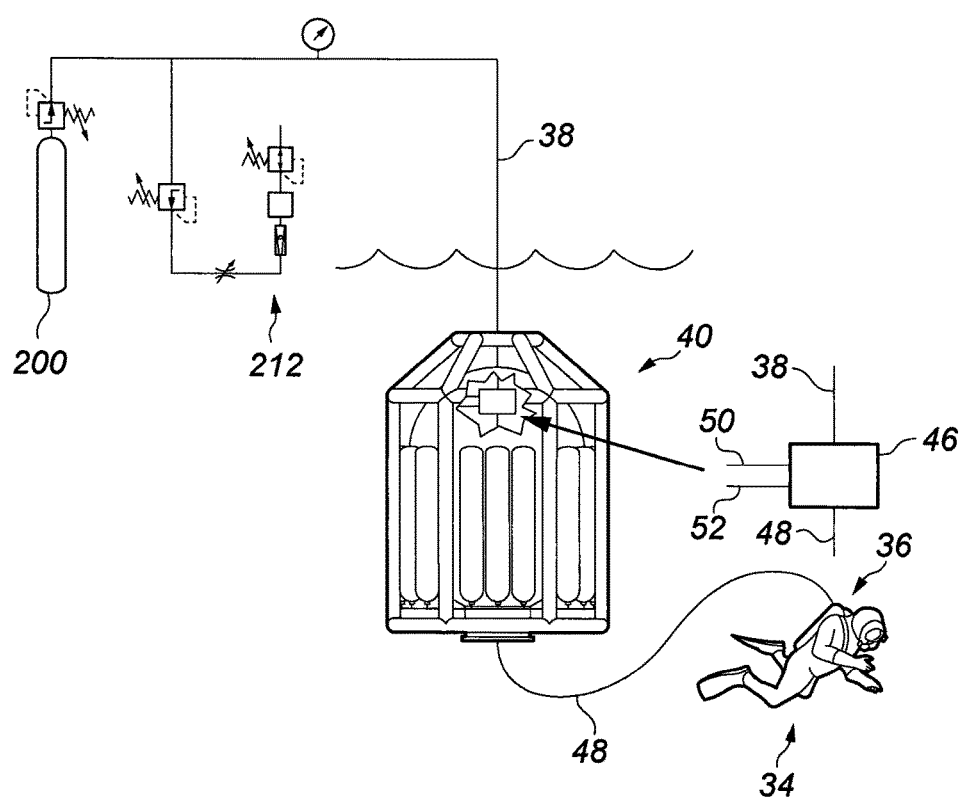
FIG. 5 is a schematic illustration of a pressure vessel, in the form of a gas storage cylinder coupled to a diving bell, and having the gas analysis system of FIG. 4.

FIG. 5 shows a further variation, in which the mixture of gasses in the tank 200 is supplied to a diving bell 40 (through the hose 38), which provides life support for the diver 34 during deployment underwater. For example, the bell 40 can be used for transferring the diver 34 from a pressure chamber at surface (the pressure of the breathing mixture in the bell 40 being set at the same level as that in the chamber), as well as for providing underwater life support for the diver during times between excursions out of the bell and into the water. Typically, the hose 38 is coupled to a gas panel 46 in the bell 40, which controls the supply of breathing gas both to an interior of the bell 40, and through a hose 48 to the breathing apparatus 36 worn by the diver 34. The gas panel 46 is also coupled to emergency breathing gas cylinders (not shown), via hoses 50 and 52, for supplying breathing gas to the interior of the bell 40 and/or to the diver 34 (via the hose 48) in the case of an emergency loss of supply of gas from the tank 200 at surface. From the above, it will be appreciated that the system 212 may effectively serve for monitoring the breathing gas supplied to both the bell 40 and to the diver's breathing apparatus 36.

Various modifications may be made to the foregoing without departing from the spirit or scope of the present invention.

For example, a saturation diving ship will typically carry large quantities of gas on board, stored in an array of large storage vessels in the form of high pressure storage cylinders. This will include pure Helium, pure Oxygen and various Heliox mixtures. Most vessels are also capable of reclaiming the gases that the diver in the water breathes out. These are then scrubbed of $CO_2$ and compressed back into one or more storage cylinders. The 'gas man' on the vessel keeps track of what is in all of the cylinders, and can blend gases to obtain the mixtures that a particular operation requires. This requires much analysis of the mixtures of gasses in a plurality of pressure vessels, which can be achieved using the system of the present invention. In basic terms, the system and method of the present invention can be used to analyse any source of pressurised gas.

The step of reducing the pressure of the portion of the mixture which is to be analysed may comprise reducing the pressure within the sensor prior to analysis. The pressure may be reduced employing a pressure control device, such as a pressure reduction valve, provided integrally with the sensor.

Reference is made particularly to problems associated with divers operating under pressure at depth. However, it will be understood that the problems associated with working under pressure, and the safe operation of pressure chambers, is not restricted to divers. Many other workers operate at pressure, including but not restricted to construction workers operating at elevated pressures in caissons and tunnels, and pressure chambers are commonly used in healthcare for a variety of hyperbaric treatments. The method and system of the present invention therefore has a use other than specifically in relation to divers operating under pressure at depth.

The invention claimed is:

1. A method of determining the partial pressure of at least one gas in a mixture of gasses contained in a pressure vessel, the mixture being pressurised to above local atmospheric pressure, in which the method comprises the steps of:
coupling a gas analysis sensor to the pressure vessel;
directing a portion of the mixture of gasses in the pressure vessel to the sensor for analysis;
reducing the pressure of the portion of the mixture which is to be analysed by the sensor to a level which is below the pressure in the vessel but above local atmospheric pressure;
operating the sensor to measure the partial pressure of the at least one gas at the reduced pressure level; and
using the partial pressure of the at least one gas, measured at the reduced pressure level, to determine the actual partial pressure of said gas in the mixture contained in the vessel by multiplying the measured pressure at the reduced pressure level by the ratio of the pressure in the vessel relative to the reduced pressure level.

2. A method as claimed in claim 1, in which the step of reducing the pressure of the portion of the mixture which is to be analysed comprises reducing the pressure prior to supply of the portion of the mixture to the sensor.

3. A method as claimed in claim 2, in which the pressure is reduced employing a pressure control device, and in which the method comprises arranging the pressure control device to provide an output at a predetermined pressure level.

4. A method as claimed in claim 1, in which the step of reducing the pressure of the portion of the mixture which is to be analysed comprises reducing the pressure within the sensor prior to analysis.

5. A method as claimed in claim 4, in which the pressure is reduced employing a pressure control device provided integrally with the sensor.

6. A method as claimed in claim 1, comprising controlling a rate of flow of the portion of the mixture through the sensor.

7. A method as claimed in claim 6, comprising throttling the flow of the mixture upstream of the sensor using a throttle, and controlling the pressure of the portion of the mixture using a back-pressure regulator downstream of the throttle.

8. A method as claimed in claim 6, comprising throttling the flow of the mixture downstream of the sensor using a throttle.

9. A method as claimed in claim 1, in which the pressure vessel is a gas storage cylinder, and in which the method comprises:
directing the mixture of gasses in the cylinder to a diver;
performing an initial reduction in the pressure of the mixture of gases directed from the cylinder to the diver to a level which is determined according to an operating depth of the diver;
and then directing the portion of the mixture of gasses to the sensor at the initially reduced pressure level.

10. A method as claimed in claim 9, in which the pressure vessel is a decompression chamber, and in which the method is a method of decompressing a person from a pressure which is above local atmospheric pressure down to local atmospheric pressure.

11. A method as claimed in claim 1, comprising locating the sensor outside the vessel, and in which the step of directing the portion of the mixture to the sensor for analysis comprises directing the portion of the mixture out of the vessel to the sensor.

12. A method as claimed in claim 1, in which the pressure of the portion of the mixture which is to be analysed is reduced to no less than about 1.5 times local atmospheric pressure.

13. A method as claimed in claim 1, in which the pressure of the portion of the mixture which is to be analysed is reduced to between about 1.5 to about 4 times local atmospheric pressure.

14. A method as claimed in claim 1, in which the pressure vessel is a life support pressure chamber, and in which the method comprises maintaining the pressure in the chamber at a substantially constant pressure over a determined period of time.

15. A method as claimed in claim 1, in which the pressure chamber is a decompression chamber, and in which the method comprises reducing the pressure of the mixture of gasses in the chamber over time in a controlled fashion, employing the determined partial pressure data.

16. A method of determining the partial pressure of at least one gas in a mixture of gasses contained in a pressure vessel, the mixture being pressurised to above local atmospheric pressure, in which the method comprises the steps of:
coupling a gas analysis sensor to the pressure vessel;
directing a portion of the mixture of gasses in the pressure vessel to the sensor for analysis;
reducing the pressure of the portion of the mixture which is to be analysed by the sensor to a level which is below the pressure in the vessel but above local atmospheric pressure;
operating the sensor to measure the partial pressure of the at least one gas at the reduced pressure level;
using the partial pressure of the at least one gas, measured at the reduced pressure level, to determine the actual partial pressure of said gas in the mixture contained in the vessel; and
determining the partial pressures of a plurality of gasses in the mixture of gasses in the vessel.

17. A method as claimed in claim 16, in which the mixture of gasses is a breathable mixture.

\* \* \* \* \*